US012766048B2

(12) United States Patent
Lipschutz et al.

(10) Patent No.: US 12,766,048 B2
(45) Date of Patent: Oct. 20, 2026

(54) DISPOSABLE HYGIENE ARTICLE WITH IMPROVED FIT

(71) Applicant: Essity Hygiene and Health Aktiebolag, Gothenburg (SE)

(72) Inventors: Oscar Lipschutz, Gothenburg (SE); Louise Eliasson, Gothenburg (SE); Sofia Ekstedt, Gothenburg (SE); Josefin Sohl, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 341 days.

(21) Appl. No.: 18/256,505

(22) PCT Filed: Dec. 29, 2020

(86) PCT No.: PCT/EP2020/087972

§ 371 (c)(1),
(2) Date: Jun. 8, 2023

(87) PCT Pub. No.: WO2022/144072

PCT Pub. Date: Jul. 7, 2022

(65) Prior Publication Data

US 2024/0099904 A1 Mar. 28, 2024

(51) Int. Cl.
*A61F 13/472* (2006.01)
*A61F 13/476* (2006.01)

(52) U.S. Cl.
CPC .............................. *A61F 13/47245* (2013.01)

(58) Field of Classification Search
CPC .............. A61F 13/472; A61F 13/47236; A61F 13/47245; A61F 13/476; A61F 2013/4706
See application file for complete search history.

(56) References Cited

U.S. PATENT DOCUMENTS 3,595,237 A 7/1971 Sargent et al.
4,500,316 A 2/1985 Damico
(Continued)

FOREIGN PATENT DOCUMENTS

CA 2339513 A1 9/2001
CN 1056048 A 11/1991
(Continued)

OTHER PUBLICATIONS

Brazil Application No. BR112023013018-2; Search Report dated Jun. 15, 2025; 4 pages.
(Continued)

*Primary Examiner* — Catharine L Anderson
(74) *Attorney, Agent, or Firm* — CANTOR COLBURN LLP

(57) ABSTRACT

The disclosure relates to a disposable hygiene article having a transverse direction, a longitudinal direction and a longitudinal centerline, the article having front, crotch and a rear portions, and including a liquid-permeable topsheet, a liquid-impermeable backsheet, and an absorbent core arranged between the topsheet and backsheet, the topsheet and backsheet extending beyond the absorbent core to provide an outer boundary region of the article that surrounds the absorbent core, the core extending between a core front edge and a core rear edge, the core including a neck region being smaller than a transverse width of the core forward of the neck region, and a transverse width rearward of the neck region, the article further including at least one asymmetrical wing wherein the asymmetrical wing outer edge meets the outer periphery of the disposable hygiene article, the outer edge of the at least one asymmetrical wing.

20 Claims, 8 Drawing Sheets

(56) References Cited

U.S. PATENT DOCUMENTS

| | | | |
|---|---|---|---|
| 5,201,727 | A | 4/1993 | Nakanishi et al. |
| 5,219,341 | A | 6/1993 | Serbiak et al. |
| 5,344,416 | A | 9/1994 | Niihara et al. |
| 5,401,268 | A * | 3/1995 | Rodier ................ A61F 13/5616 604/383 |
| 5,429,630 | A | 7/1995 | Beal et al. |
| 5,462,166 | A | 10/1995 | Minton et al. |
| 5,484,636 | A | 1/1996 | Berg |
| 5,733,274 | A | 3/1998 | Osborn, III |
| 6,013,062 | A | 1/2000 | Dilnik |
| 6,293,932 | B1 | 9/2001 | Balzar et al. |
| 6,447,495 | B1 | 9/2002 | Luizzi et al. |
| 6,554,812 | B2 | 4/2003 | Drevik |
| 6,569,138 | B2 | 5/2003 | Helmfridsson et al. |
| 6,616,643 | B1 | 9/2003 | Costa |
| 6,746,435 | B1 | 6/2004 | Van Tilburg |
| 6,866,658 | B2 * | 3/2005 | Drevik .............. A61F 13/47245 604/385.31 |
| 6,945,967 | B2 | 9/2005 | Drevik et al. |
| 6,964,655 | B2 | 11/2005 | Killeen et al. |
| 7,059,474 | B2 | 6/2006 | Tippey |
| 7,078,583 | B2 | 7/2006 | Kudo et al. |
| 7,312,372 | B2 | 12/2007 | Miyama et al. |
| 7,727,213 | B2 | 6/2010 | Nomoto et al. |
| 7,922,706 | B2 | 4/2011 | Konawa |
| 8,237,012 | B2 | 8/2012 | Miyama et al. |
| 8,986,273 | B2 | 3/2015 | Mercer |
| 8,993,832 | B2 | 3/2015 | Kuroda et al. |
| 9,114,044 | B2 | 8/2015 | Yoshiba |
| 9,173,786 | B2 | 11/2015 | Roh et al. |
| 9,566,196 | B2 | 2/2017 | Carlucci et al. |
| 9,775,752 | B2 | 10/2017 | Park et al. |
| 10,258,513 | B2 * | 4/2019 | Kuramochi ......... A61F 13/4704 |
| 11,000,431 | B2 | 5/2021 | Blomström et al. |
| 11,058,591 | B2 * | 7/2021 | Vohwinkel ........... A61F 13/476 |
| 11,065,161 | B2 | 7/2021 | Blomström |
| 11,246,770 | B2 | 2/2022 | Vohwinkel et al. |
| 11,357,672 | B2 | 6/2022 | Yonaha |
| 12,239,513 | B2 | 3/2025 | Schmoker et al. |
| 2003/0083637 | A1 | 5/2003 | Killeen et al. |
| 2003/0208177 | A1 | 11/2003 | D'Alessio et al. |
| 2004/0138636 | A1 | 7/2004 | Cardin et al. |
| 2004/0243087 | A1 | 12/2004 | Kinoshita et al. |
| 2005/0283131 | A1 * | 12/2005 | Zander .................. A61F 13/476 604/385.04 |
| 2006/0271003 | A1 | 11/2006 | Loescher |
| 2008/0312624 | A1 | 12/2008 | Hundorf et al. |
| 2009/0292268 | A1 | 11/2009 | Bagger-Sjöbäck et al. |
| 2011/0009844 | A1 | 1/2011 | Toro et al. |
| 2011/0092944 | A1 | 4/2011 | Sagisaka et al. |
| 2012/0109093 | A1 | 5/2012 | Wilson et al. |
| 2012/0259306 | A1 | 10/2012 | Petersen |
| 2012/0316533 | A1 | 12/2012 | Norimoto |
| 2013/0123731 | A1 | 5/2013 | Mercer et al. |
| 2013/0310784 | A1 | 11/2013 | Bryant et al. |
| 2015/0018795 | A1 | 1/2015 | Park et al. |
| 2015/0272791 | A1 | 10/2015 | Hsieh et al. |
| 2016/0235607 | A1 | 8/2016 | Mercer et al. |
| 2017/0354549 | A1 | 12/2017 | Cho et al. |
| 2018/0325750 | A1 | 11/2018 | Vohwinkel et al. |
| 2018/0325751 | A1 | 11/2018 | Vohwinkel et al. |
| 2018/0325753 | A1 | 11/2018 | Vohwinkel |
| 2018/0325754 | A1 | 11/2018 | Vohwinkel et al. |
| 2019/0374396 | A1 | 12/2019 | Hood et al. |
| 2020/0129347 | A1 | 4/2020 | Blomström et al. |
| 2020/0138642 | A1 | 5/2020 | Wagner et al. |
| 2020/0138643 | A1 | 5/2020 | Hanson et al. |
| 2020/0138644 | A1 | 5/2020 | Hanson et al. |
| 2020/0155364 | A1 | 5/2020 | Rönnberg et al. |
| 2020/0155365 | A1 | 5/2020 | Blomström |
| 2020/0163809 | A1 | 5/2020 | Radne et al. |
| 2020/0281779 | A1 | 9/2020 | Kalentun |
| 2020/0368083 | A1 | 11/2020 | Rönnberg et al. |
| 2021/0220189 | A1 | 7/2021 | Miao et al. |
| 2022/0000683 | A1 | 1/2022 | Ekstedt et al. |
| 2022/0008261 | A1 | 1/2022 | Ekstedt et al. |
| 2023/0022804 | A1 | 1/2023 | Pollard |
| 2023/0240914 | A1 | 8/2023 | Blomström et al. |
| 2023/0363957 | A1 | 11/2023 | Lipschutz et al. |
| 2025/0213402 | A1 | 7/2025 | Dahl et al. |
| 2025/0381076 | A1 | 12/2025 | Sohl et al. |

FOREIGN PATENT DOCUMENTS

| | | | |
|---|---|---|---|
| CN | 1073090 | A | 6/1993 |
| CN | 1203520 | A | 12/1998 |
| CN | 1312060 | A | 9/2001 |
| CN | 1315168 | A | 10/2001 |
| CN | 1498608 | A | 5/2004 |
| CN | 1329010 | C | 8/2007 |
| CN | 101878011 | A | 11/2010 |
| CN | 101999964 | A | 4/2011 |
| CN | 203815725 | U | 9/2014 |
| CN | 203915242 | U | 11/2014 |
| CN | 204501249 | U | 7/2015 |
| CN | 105188626 | A | 12/2015 |
| CN | 105455962 | A | 4/2016 |
| CN | 106488760 | A | 3/2017 |
| CN | 206102848 | A | 4/2017 |
| CN | 106794099 | A | 5/2017 |
| CN | 107427402 | A | 12/2017 |
| CN | 110198694 | A | 9/2019 |
| CN | 110709043 | A | 1/2020 |
| CN | 110709044 | A | 1/2020 |
| CN | 110730651 | A | 1/2020 |
| CN | 110831555 | A | 2/2020 |
| CN | 110831556 | A | 2/2020 |
| CN | 110913814 | A | 3/2020 |
| CO | 5160278 | A1 | 5/2002 |
| CO | 2020000045 | A2 | 1/2020 |
| CO | 2020000079 | A2 | 1/2020 |
| CO | 2021006995 | A2 | 6/2021 |
| CO | 2021007051 | A2 | 6/2021 |
| EP | 0471385 | A1 | 2/1992 |
| EP | 0549784 | A1 | 7/1993 |
| EP | 0674500 | A1 | 10/1995 |
| EP | 0983760 | A1 | 3/2000 |
| EP | 1138294 | A1 | 10/2001 |
| EP | 1208823 | A1 | 5/2002 |
| EP | 0857051 | B1 | 7/2003 |
| ES | 2230013 | T3 | 5/2005 |
| JP | H05506799 | A | 10/1993 |
| JP | H0586322 | U | 11/1993 |
| JP | H07506037 | A | 7/1995 |
| JP | H09253131 | A | 9/1997 |
| JP | 2009213719 | A | 9/2009 |
| JP | 2010227241 | A | 10/2010 |
| JP | 2011045608 | A | 3/2011 |
| JP | 2012213420 | A | 11/2012 |
| JP | 2013220225 | A | 10/2013 |
| JP | 2014150878 | A | 8/2014 |
| JP | 2014223216 | A | 12/2014 |
| JP | 2015100502 | A | 6/2015 |
| JP | 2016104089 | A | 6/2016 |
| JP | 2017006470 | A | 1/2017 |
| JP | 2017503624 | A | 2/2017 |
| JP | 2017176742 | A | 10/2017 |
| JP | 2019097898 | A | 6/2019 |
| JP | 2020526284 | A | 8/2020 |
| KR | 20050008509 | A | 1/2005 |
| RU | 2277891 | C2 | 6/2006 |
| WO | 9116873 | A1 | 11/1991 |
| WO | 9301781 | A1 | 2/1993 |
| WO | 9413236 | A1 | 6/1994 |
| WO | 9855063 | A1 | 12/1998 |
| WO | 0021477 | A1 | 4/2000 |
| WO | 0172254 | A2 | 10/2001 |
| WO | 2010110270 | A1 | 9/2010 |
| WO | 2013094779 | A1 | 6/2013 |
| WO | 2016068957 | A1 | 5/2016 |
| WO | 2018226132 | A1 | 12/2018 |
| WO | 2018226134 | A1 | 12/2018 |
| WO | 2019007527 | A1 | 1/2019 |
| WO | 2019007529 | A1 | 1/2019 |

(56) References Cited

FOREIGN PATENT DOCUMENTS

| | | | | |
|---|---|---|---|---|
| WO | 2019008090 A1 | 1/2019 | | |
| WO | 2019008091 A1 | 1/2019 | | |
| WO | WO-2019039976 A1 * | 2/2019 | ......... | A61F 13/4753 |
| WO | 2019112641 A1 | 6/2019 | | |
| WO | 2022144071 A1 | 7/2022 | | |
| WO | 2022144073 A1 | 7/2022 | | |

OTHER PUBLICATIONS

Non-Final Office Action issued in U.S. Appl. No. 18/256,523 dated Nov. 9, 2023; 23 pages.
Non-Final Office Action issued in U.S. Appl. No. 18/256,623 dated Mar. 21, 2024.
Chinese Application No. 202080108180.9; Office Action with English translation dated Aug. 28, 2024; 14 pages.
Chinese Application No. 202080107950.8; Office Action with English translation dated Dec. 27, 2024; 16 pages.
Chinese Application No. 202080108282.0; Office Action with English translation dated Aug. 27, 2024; 21 pages.
Final Office Action issued U.S. Appl. No. 18/256,523 dated May 2, 2024.
Chinese Application No. 202080107950.8; Office Action with English translation dated Aug. 28, 2024; 17 pages.
International Search Report & Written Opinion for International Application No. PCT/EP2020/087970; International Filing Date: Dec. 29, 2020; Date of Mailing: Sep. 17, 2021; 13 pages.
International Search Report & Written Opinion for International Application No. PCT/EP2020/087972; International Filing Date: Dec. 29, 2020; Date of Mailing: Sep. 24, 2021; 13 pages.
International Search Report & Written Opinion for International Application No. PCT/EP2020/087973; International Filing Date: Dec. 29, 2020; Date of Mailing: Oct. 7, 2021; 11 pages.
Brazil Application No. BR112023012912-5; Search Report dated Jun. 15, 2025; 4 pages.
Chinese Application No. 202080107950.8; Office Action with English translation dated May 22, 2025; 19 pages.
U.S. Appl. No. 18/256,598; Non-Final Office Action dated Sep. 10, 2025; 57 pages.
Advisory Action issued in U.S. Appl. No. 18/256,523 dated Feb. 13, 2024; 6 pages.
Non-Final Office Action issued in U.S. Appl. No. 18/256,523 dated Mar. 21, 2024.
US Non-Final Office Action, U.S. Appl. No. 18/843,959, mailed Jun. 29, 2026, 52 pages.
Extended European Search Report for European Application No. 19955481.7; Report Mail Date Jun. 30, 2023 (5 Pages).
Office Action issued in U.S. Appl. No. 16/626,672 dated Jul. 11, 2024.
U.S. Final Office Action for U.S. Appl. No. 16/626,039, filed Dec. 23, 2019; Report Mail Date Dec. 12, 2023 (29 Pages).
U.S. Final Office Action for U.S. Appl. No. 16/626,672, filed Dec. 26, 2019; Report Mail Date Nov. 20, 2023 (30 Pages).
Australian Government, IP Australia, Office Action issued in AU Application No. 2017422549, dated Apr. 21, 2020 (4 pages).
Chinese Application No. 201980102566.6; Office Action dated Aug. 3, 2022; 14 pages. with English Abstract.
Chinese Application No. 201980102571.7; Office Action dated Aug. 8, 2022; 19 pages, with English Abstract.
Colombia Office Action for Columbian Application No. NC2022/0008163; Report Mail Date Jul. 24, 2024 (30 Pages; with English Translation).
Colombia Patent Application No. NC2023/0008638; Office Action with English translation dated Oct. 10, 2025; 23 pages.
Colombian Patent Office, Office Action issued in CO application No. NC2020/0000068 dated Jul. 16, 2021 with English explanation of rejections/relevance from local counsel (11 pages).
Colombian Patent Office, Office Action issued in CO application No. NC2020/0000068 dated Nov. 30, 2021 (10 pages).
Columbian Office Action, Application No. PCT/EP2020/087973, mailed Nov. 20, 2025; with English Translation, 28 pages.
Columbian Office Action, International Application No. PCT/EP2020/087970, mailed Dec. 4, 2025; with English Translation, 22 pages.
Mexican Application Office Action for Mexican Application No. MX/a/2019/015545; Report Mail Date Apr. 17, 2023 (5 Pages; with English translation).
Egypt Office Action, Application No. 2023050817, mailed Oct. 2025, with English Translation, 22 pages.
Egyptian Patent Office, Office Action issued in application No. 2019121986, 5 pages.
International Preliminary Report on Patentability for International Application No. PCT/EP2017/067068, dated Oct. 25, 2019, 18 pages.
International Preliminary Report on Patentability for International Application No. PCT/EP2017/067071, dated Oct. 25, 2019, 21 pages.
International Preliminary Report on Patentability for International Application No. PCT/EP2018/068232, dated Oct. 23, 2019, 21 pages.
International Preliminary Report on Patentability for International Application No. PCT/EP2018/068233, dated Oct. 21, 2019, 16 pages.
International Search Report & Written Opinion for International Application No. PCT/EP2022/058785; International Filing Date: Apr. 1, 2022; Date of Mailing: Nov. 18, 2022; 10 pages.
International Search Report & Written Opinion for International Application No. PCT/EP2022/069219; International Filing Date: Jul. 11, 2022; Date of Mailing: Feb. 6, 2023; 9 pages.
International Search Report and Written Opinion for International Application No. PCT/EP2017/067068, dated Jan. 8, 2018, 15 pages.
International Search Report and Written Opinion for International Application No. PCT/EP2017/067071, dated Jan. 8, 2018, 20 pages.
International Search Report and Written Opinion for International Application No. PCT/EP2018/068232, dated Aug. 16, 2018, 17 pages.
International Search Report and Written Opinion for International Application No. PCT/EP2018/068233, dated Aug. 17, 2018, 17 pages.
International Serach Report & Written Opinion for International Application No. PCT/SE2019/051281; International Filing Date: Dec. 13, 2019; Date of Mailing: Jul. 20, 2020; 15 pages.
International Serach Report & Written Opinion for International Application No. PCT/SE2019/051282; International Filing Date: Dec. 13, 2019; Date of Mailing: Jul. 20, 2020; 13 pages.
Japanese Patent Office, Office Action issued in JP 2020-500043 dated Mar. 31, 2021 with English translation, 17 pages.
Japanese Patent Office, Office Action issued in JP 2020-500129 dated Mar. 31, 2021 with English translation, 18 pages.
Japanese Patent Office, Office Action issued in JP Application No. 2020-500068, dated Feb. 2, 2021 with partial English Translation (14 pages).
Japanese Patent Office, Office Action issued in JP Application No. 2020-500117, dated Feb. 1, 2021 with partial English Translation, 14 pages.
Malaysian Application No. PI2020000003; Malaysian Search Report dated May 27, 2022; 2 pages.
Merriam-Webster Dictionary, "Upside Down Definition & Meaning" https://www.merriam-webster.com/dictionary/upside%down (Year 2023).
National Intellectual Property Administration (CNIPA) of the People's Republic of China, First Office Action issued in CN Application No. 20170092879.9, dated Mar. 17, 2021 with English translation, 24 pages.
National Intellectual Property Administration (CNIPA) of the People's Republic of China, First Office Action, Application No. 201880044787.8, dated Apr. 20, 2020 and English Translation (13 pages).
National Intellectual Property Administration (CNIPA) of the People's Republic of China, Office Action issued in CN 201780092880.1 dated Mar. 29, 2021 with English Translation, 20 pages.
Non-Final Office Action issued in U.S. Appl. No. 17/783,943, dated Feb. 16, 2024 (22 Pages).

(56) References Cited

OTHER PUBLICATIONS

Office Action issued in Colombia Application No. NC2022/0008157 dated May 8, 2024.
Russian Patent Office, Decision to Grant issued in RU application No. 2019139865/(078371), dated Jul. 7, 2020 with English translation (21 pages).
Russian Patent Office, Decision to Grant issued in RU Application No. 219139870/03(078379), dated Jun. 25, 2020 with English Translation (22 pages).
U.S. Appl. No. 16/626,039; Notice of Allowance dated Jul. 23, 2024; 12 pages.
U.S. Appl. No. 16/626,039; Notice of Allowance dated Jun. 5, 2024; 15 pages.
U.S. Appl. No. 16/626,039; Notice of Allowance dated Sep. 27, 2024; 12 pages.
U.S. Final Office Action for U.S. Appl. No. 17/783,943, filed Jun. 9, 2022; Report Mail Date Aug. 7, 2023 (pp. 1-15).
U.S. Non-Final Office Action for U.S. Appl. No. 17/783,943, filed Jun. 9, 2022; Report Mail Date Jun. 1, 2023 (pp. 1-16).
U.S. Office Action for U.S. Appl. No. 16/626,039, filed Dec. 23, 2019; Report Mail Date Aug. 3, 2023 (pp. 1-19).
U.S. Office Action for U.S. Appl. No. 16/626,672, filed Dec. 26, 2019; Report Mail Date Jul. 27, 2023 (pp. 1-21).
U.S. Appl. No. 17/783,533, filed Jun. 8, 2022, Non-Final Office Action mailed Jan. 16, 2025, 16 pages.
U.S. Appl. No. 18/256,598, filed Jun. 8, 2023, Final Office Action Dated Jan. 8, 2026, 17 pages. U.S. Appl. No. 18/256,598, filed Jun. 8, 2023, Final Office Action Dated Jan. 8, 2026, 17 pages.

* cited by examiner

DISPOSABLE HYGIENE ARTICLE WITH IMPROVED FIT

CROSS REFERENCE TO RELATED APPLICATIONS

This application is a National Stage application of PCT/EP2020/087972, filed Dec. 29, 2020, which is incorporated by reference in its entirety herein.

TECHNICAL FIELD

The present invention relates to disposable hygiene articles, such as sanitary towels, panty liners and incontinence pads that are designed so that they adopt a particular form when in use to provide improved fit and security against leakage.

BACKGROUND ART

Disposable hygiene articles need to have good absorptive properties, comfort and need to provide a sense of leakage security and good fit for a user. Various designs and methods have been employed in hygiene articles so that they could follow the contours of the user's body well and do not move out of place during use.

However, there is still a need to further improve the fit of the article and how the article conforms to the body of the user.

SUMMARY OF THE INVENTION

It has been found that despite prior art solutions for disposable hygiene articles, there is still a need to improve the fit of the article, especially the manner in which the article conforms to the body of the user. There is a need to better control how the article bends and conforms to the body, especially in respect of the crotch region and the front part of the article. For comfort and security against leakage, it is important that the article deforms in a predictable manner to fit the anatomy of the user and that the wings are positioned such that they do not hinder the adaptation of the article to the user's anatomy. It is also of importance that existing manufacturing equipment and methods can be used for the manufacture of the articles with minimal modification.

One of the objectives of the present disclosure is thus to provide a disposable hygiene article with improved fit of the article and an improvement in the manner and consistency with which the article conforms to the body of a user. In particular, the present invention aims to provide an improved fit in the front and crotch portion of the article. Improved leakage security due to optimal positioning of the wings around the user's underwear to obtain a more forward placement of the article is also desirable.

A further objective of the present disclosure is to provide an article with improved comfort for the user, whilst maintaining absorbency that is satisfactory or improving absorbency. The disposable hygiene article may be a sanitary towel, a panty liner, an incontinence pad, or an insert provided with wings for folding around the edges of the crotch portion.

The above objectives may be achieved by the present disposable hygiene article as defined in the appended claims. Further advantages provided by the present disclosure will be apparent to the skilled person in light of the following description of the invention.

In a first aspect of the invention, there is provided: a disposable hygiene article having a transverse direction, a longitudinal direction and a longitudinal centre line dividing the article into left-hand and right-hand portions. The article has a front portion, a crotch portion and a rear portion, and comprises a liquid-permeable topsheet, a liquid-impermeable backsheet and an absorbent core arranged between the topsheet and the backsheet. The topsheet and the backsheet extend beyond the absorbent core to provide an outer boundary region of the article that surrounds the absorbent core.

An outer contour of the absorbent core is defined by mutually symmetric mirror-imaged portions, arranged symmetrically about the longitudinal centerline, and defined by symmetrical left and right core edge lines. The absorbent core is also delimited by a core front edge in the front portion and a core rear edge in the rear portion.

In some embodiments, the left and right hand portions of the disposable hygiene article (including the absorbent core, topsheet, backsheet, including the wings) are symmetrical about the longitudinal centerline. However, in other embodiments, the absorbent core can be symmetrical about the longitudinal centerline, whilst the wings may be provided in an asymmetrical manner. Moreover, by "mutually symmetrical" and "mirror-imaged" it will be understood that each portion may be substantially symmetrical, and that minor or inconsequential deviations from a perfect mirror image fall within the scope of the invention.

The absorbent core comprises a neck region at which the transverse width between the left and right core edge lines is smaller than a transverse width of the core forward of the neck region, and a transverse width rearward of the neck region. The portion of the core forward of the neck region is defined as the head region of the core and the portion of the core rearward of the neck is defined as the body portion.

The shape and construction of the core can be further adapted to optimize fit, absorbency, and fluid distribution. For example, the profile of the core can be formed such that it comprises a head part and two leg portions extending symmetrically about the centre line in a longitudinal direction of the article.

The disposable hygiene article further comprises at least one asymmetrical wing as seen along any transverse axis of the disposable hygiene article. The asymmetrical wing comprises an outer edge extending in an outward direction from the outer periphery of the disposable hygiene article, the outer edge meeting the outer periphery of the disposably hygiene article at front and rear wing junctions connected via a wing junction line $J_w$. The outer edge of the at least one asymmetrical wing comprises a front wing distance point $D_f$ and a rear wing distance point $D_r$, wherein the front wing distance point is being spaced from the junction line $J_w$ in an outboard transverse direction by a transverse distance J1 of 3 mm. Further, the front wing distance point $D_f$ is spaced from the neck in a rearward longitudinal direction by a first longitudinal distance D1 of between 5-30 mm, more preferably between 10-25 mm and most preferably between 17-20 mm.

The at least one asymmetrical wing may be formed with an outer edge comprising a wing positioning profile coinciding with a section of the outer edge. The wing positioning profile is formed from a wave having a baseline $X_{wp}$ and a longitudinal axis $Y_{wp}$ perpendicular to the baseline $X_{wp}$, the wave starting from the front wing junction and extending outwards. The wave consists of a concave curve having a trough and a convex curve having a peak. Further, the wing positioning profile ends at a wing positioning profile end point where said wave no longer coincides with said outer edge. The presence of the trough provides for more maneuvering room when folding the wing along the longitudinal side edge of the crotch portion. The peak of the wing positioning profile provides a "perception of forward direction", a visual cue to the user to place the disposable hygiene article more forward in the underwear such that the point of wetness is most optimally placed in relation to the user's anatomy. In addition, the peak of the convex curve provides for an intuitive wing handling portion that facilitates grasping of the wing.

The wing junction line $J_W$ corresponds to the wing length and may be between 50-110 mm, preferably between 75-100 mm, and most preferably between 85-95 mm. Such a wing length provides for an optimal balance between folding of the wings and providing protection against leakage from the sides.

The presence of the neck region promotes shaping of the disposable hygiene article in a manner that more closely approximates the anatomy of the user, especially in a crotch and front portion of the article. In particular, the presence of the neck region enhances bending of the front portion towards the pubic area of the user. In this respect, the width M between the left and right core edge lines in the neck region may be between 30-60 mm, preferably between 32-42 mm to provide for optimal folding of the disposable hygiene article.

The front wing junction width $W_{fwj}$; between the left and the right front wing junctions, as seen along the transverse axis, may be between 75-95 mm, more preferably between 80-90 mm, and most preferably between 85-87 mm. The rear wing junction width $W_{rwj}$ between the left and the right rear wing junctions, as seen along the transverse axis, may be between 85-95 mm, more preferably between 87-93 mm, and most preferably between 88-91 mm. The configuration described above allows the disposable hygiene article to optimally cover leakage in the crotch portion. Optionally, the rear wing junction width may be larger than the front wing junction width to more closely conform to the shape of the user's underwear.

The peak of the convex curve of the wing positioning profile may be located forward of the through of the concave curve as seen in the longitudinal direction y. Such a configuration further emphasizes the "sense of forward direction" and thus further promotes a forward placement of the disposable hygiene article.

The baseline $X_{wp}$ of the wave of the wing positioning profile may be placed perpendicular on the longitudinal centerline A of the disposable hygiene article to provide for optimal maneuvering room for folding of the wings.

The distance W2 between the front wing distance point $D_{fr}$ and the peak of the convex curve of the wing positioning profile, as measured along the baseline $X_{wp}$, may be between 8-30 mm, preferably between 10-25 mm, and most preferably between 10-20 mm. The distance W1 between the front wing distance point and the wing positioning profile end point, as measured along the baseline $X_{wp}$, may be between 13-35 mm, preferably between 16-25 mm.

The height H between the trough of concave curve and the peak of the convex curve of the wave, as measured along the longitudinal axis $Y_{wp}$ of the wave may be between 1-5 mm.

The disposable hygiene article may be configured such that the wing defines an imaginary straight line N along a section of the wing positioning profile, the imaginary straight line N starting from the trough of the concave curve and extending outboard, wherein the imaginary straight line N defines and angle θ with respect to a straight line w starting from the trough of the concave cure and running parallel to the baseline $X_{wp}$, the magnitude of the angle θ being between +5 and +25 degrees, preferably between +8 and +20 degrees and most preferably between +10 and +17 degrees. Alternatively, the magnitude of the angle θ may be between −5 and −25 degrees, preferably between −8 and −20 degrees and most preferably between −10 and −17 degrees.

Furthermore, the wing may be formed with an outer edge which defines at least one arc of a circle coinciding with a section of the outer edge and having a defined radius, said section extending between a first point on the outer edge and a second point along said outer edge where said arc no longer coincides with said outer edge, and wherein said radius is within the interval of 40-500 mm. The presence of an arc-shaped outer edge as minimizes the risk that a user folds a wing over the other wing during use such that the adhesive on the first wing is positioned on the second wing.

The outer edge may define two or more arcs of a circle, each of said arcs defining a curve-shaped section and having a defined radius, said first radius and said second radius both being within the interval of 40-500 mm.

Furthermore, said outer edge may include at least one straight section. According to the present disclosure a straight section is defined as a section which defines a curve-shaped section having a radius being above 600 mm.

The wing may be configured to define a lower straight line along a lower edge section, wherein the lower straight line defines an angle α1 with respect to a transverse axis X1 perpendicular to the longitudinal centerline A, the magnitude of the angle α1 may be between 30-60 degrees. This enables the creation of wings with a longer wing length which minimizes the risk of leakage along the longitudinal side edges and contributes to the perception of forward direction. In an alternative embodiment, the angle α1 may be between 5-30 degrees which allows for a more defined folding line such that the user may more easily fold the wings of the disposable hygiene article 1 around the crotch region of the underwear.

The disposable hygiene article according to the present disclosure may further comprise a second asymmetrical wing as seen along any transverse axis of the disposable hygiene article, wherein the first and the second asymmetrical wing are asymmetrical with respect to each other as seen along the longitudinal centerline. By providing a disposable hygiene article with asymmetrical wings as described above, the extension of the fastening wings in the transverse direction may be increased without having the problem of the wings overlapping each other during use.

BRIEF DESCRIPTION OF THE DRAWINGS

The present invention will be further explained hereinafter by means of non-limiting examples and with reference to the appended drawing wherein.

DETAILED DESCRIPTION

The present disposable hygiene article is an absorbent article aimed for personal hygiene and may be for example a sanitary towel, a panty liner, or an incontinence pad. Such articles are commonly used for acquisition and storage of bodily exudates such as urine, faeces or menstrual fluid. The absorbent article is disposable, which means that it is intended to be used only once and disposed thereafter, rather than being cleaned and re-used. The absorbent article may suitably be a sanitary towel, and the design of the article is particularly suitable for sanitary towels.

Figure 1:
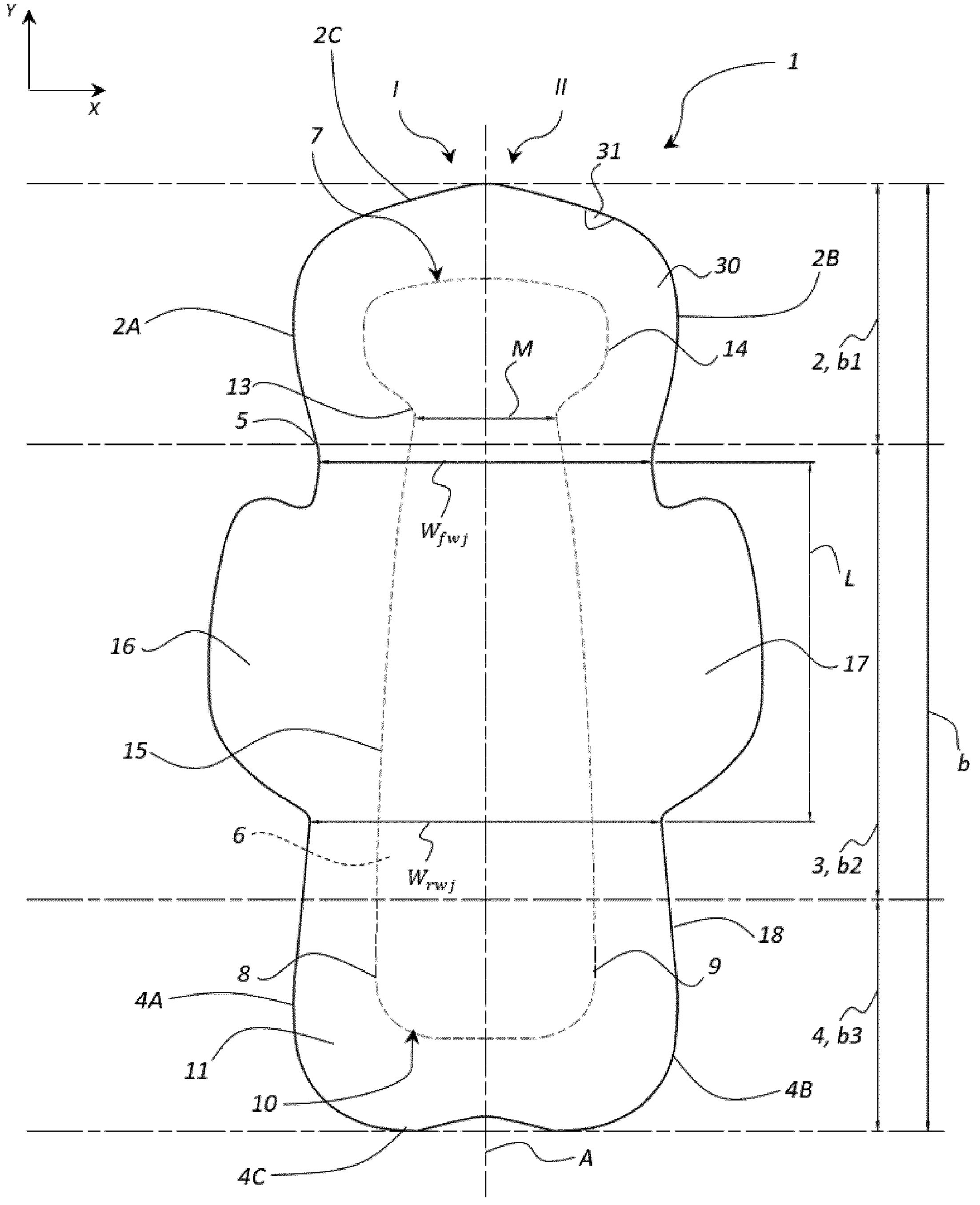
FIG. 1 shows schematically a plan view of an exemplary disposable hygiene article according to the present disclosure.

FIG. 1 shows a plan view of an article 1 according to the disclosure. The article 1 shown in FIG. 1 is a sanitary towel. The article 1 has a transverse direction x, a longitudinal direction y and a longitudinal centre line A. The longitudinal centre line A divides the article into left- and right-hand mirror-image halves, I, II, which may be symmetrical in shape about the lnogitudinal centerline A. By the expression "symmetrical about the longitudinal centre line A" it is herein meant that each point in the article on first longitudinal portion I on a first side of the longitudinal centre line A has a corresponding point in the article on the second longitudinal portion II on the other side of the longitudinal centre line A; the two points being related to each other by reflection in a plane located on the longitudinal centre line A.

The article 1 comprises a front portion 2, a crotch portion 3, and a rear portion 4. The article 1 comprises a liquid-permeable topsheet 30, a liquid-impermeable backsheet 31, and an absorbent core 6 arranged between the topsheet 30 and the backsheet 31. The surface area of the topsheet 30 and the backsheet 31 extends beyond the surface area of the absorbent core 6 to provide for an outer boundary region 11 of the article surrounding the absorbent core 6. An outer contour of the absorbent core 6 is defined by mirror-imaged left and right core edge lines 8, 9, and the absorbent core 6 is delimited by a core front edge 7 in the front portion 2 and a core rear edge 10 in the rear portion 4.

The front portion 2 comprises a pair of front portion longitudinal side edges 2A and 2B which are connected by a front end edge 2C. The front portion longitudinal side edges 2A and 2B in FIG. 1 are curved and bulge outwards with respect to the longitudinal centerline A, thus following the contour of the panty. Alternatively, the front portion longitudinal side edges 2A and 2B may be substantially parallel to the longitudinal centerline. In FIG. 1, the frond end edge 2C tapers towards and apex. Similar to the front portion 2, the rear portion 4 also comprises a pair of rear portion longitudinal side edges 4A and 4B which are connected by a rear end edge 4C. The rear portion longitudinal side edges 4A and 4B are inclined inwards towards the crotch portion 4. A middle part of the rear end edge 4C of the article 1 bulges inwards. The combination of the apexed front end edge 2C and an inwards bulging rear end edge 4C helps the user to more easily identify the front and the back of the article 1.

As shown in FIG. 1, the core 6 comprises neck region 13 having a narrowest width M (as measured in the transverse direction x between the left and right core edge lines (8, 9)) which is narrower than a transverse width of the core forward of the neck region, and a transverse width rearward of the neck region as measured in the transverse direction x between the first and the second core edge lines (8, 9). The narrowest width M is located in the front portion 2 of the core 6 or at a location of a transition 5 between the front portion 2 of the core and the crotch portion 3 of the core. The portion of the core forward of the neck region is defined as a head region 14 of the core and the portion of the core rearward of the neck is defined as the body portion 15.

The article 1 further comprises a left and a right wing 16, 17 extending outboard from the longitudinal side edges (8, 9) of the outer periphery 18 of the disposable hygiene article 1. As shown if FIG. 3, the outer edges of the left and right wing meet the outer periphery 18 of the disposable hygiene article 1 in the front part of the crotch region 3 at the front left wing junction 19 and the right front wing junction 20, respectively. In the rear part of the crotch region 3, the outer edges of the left and right wing 16, 17 meet the outer periphery 18 of the disposable hygiene article at the rear left wing junction 21 and the rear right wing junction 22, respectively.

Figure 3:
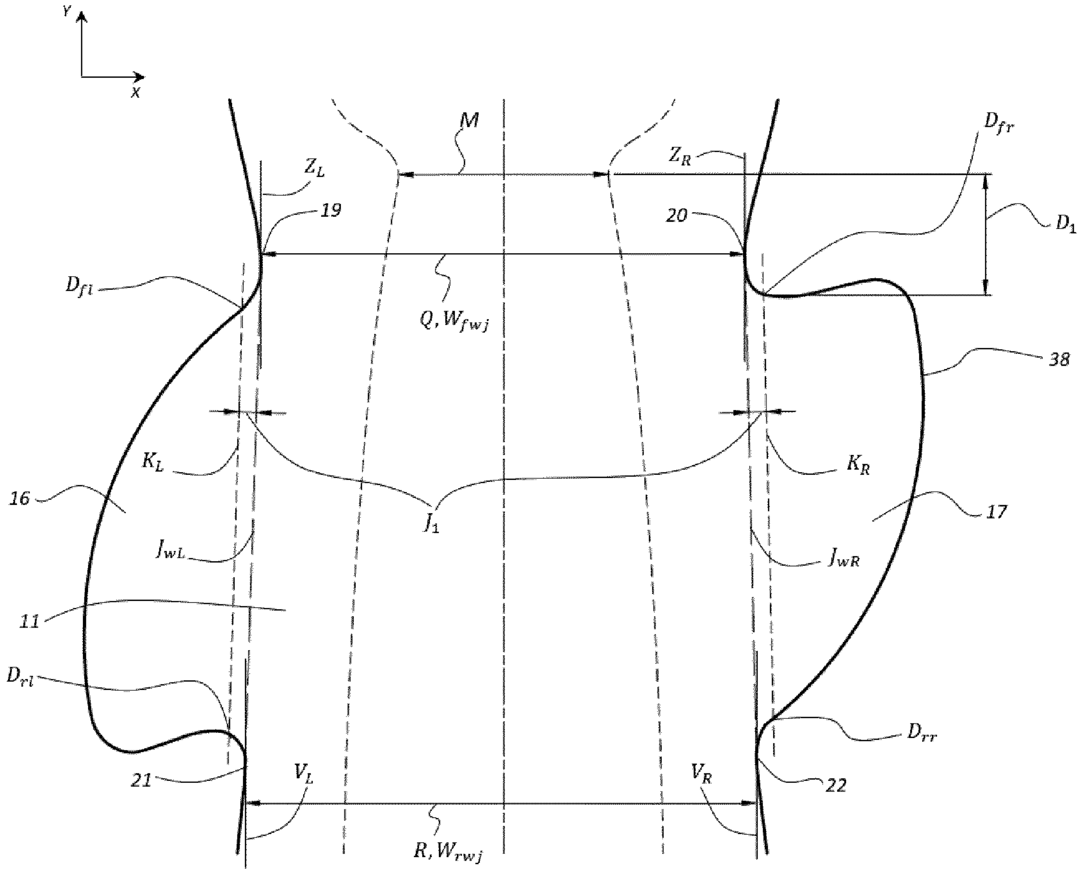
FIG. 3 shows schematically an enlarged view of a portion of an exemplary disposable hygiene article according to the present disclosure.

In the context of this application, the front wing junctions 19, 20 and the rear wing junctions 21, 22 are defined as follows and with reference to FIG. 3. In the crotch portion 3, an imaginary longitudinal straight line $Z_{L,R}$ is drawn such that it touches the outer periphery 18 at the narrowest width Q in the transverse direction of the disposable hygiene article 1 forward of the left and right wing 16, 17. The intersection between the imaginary straight line $z_L$ forward of the left wing 16 and the outer periphery 18 is defined as the front left wing junction 19, whereas the intersection between the imaginary straight line $z_R$ forward of the right wing 17 and the outer periphery 18 is defined as the front right wing junction 20. In embodiments where the imaginary straight line $Z_L$, $Z_R$ coincides with the longitudinal side edges of the outer periphery 1 (e.g. because the longitudinal side edges of the outer periphery consist of straight lines), the front wing junctions 19 and 20 are defined as the point located on the section of the imaginary straight line $Z_{L,R}$ coinciding with the outer periphery, being most closely located in the forward direction to the wing of the disposable hygiene article. The rear wing junctions 21, 22 are defined by drawing an imaginary longitudinal straight line $V_{L,R}$ such that it touches the outer periphery 18 at the narrowest width R in the transverse direction of the disposable hygiene article 1 rearward of the left and right wing 16, 17. The intersection between the imaginary straight line $V_L$ rearward of the left wing 16 and the outer periphery 18 is defined as the rear left wing junction 21, whereas the intersection between the imaginary straight line $V_R$ rearward of the right wing 17 and the outer periphery 18 is defined as the rear right wing junction 22. In embodiments where the imaginary straight line $V_L$, $V_R$ coincides with the longitudinal side edges of the outer periphery 1 (e.g. because the longitudinal side edges of the outer periphery consist of straight lines), the rear wing junctions 21 and 22 are defined as the point located on the section of the imaginary straight line coinciding with the outer periphery, being most closely located in the rearward direction to the wing of the disposable hygiene article. As shown in FIG. 3, the imaginary left wing junction line $J_{wL}$ connects the front left wing junction 19 with the rear left wing junction 21, while the imaginary right wing junction line $J_{wR}$ connects the front right wing junction 20 with the rear right wing junction 22. In the context of this application, the left and right wing junction lines $J_{wL}$ and $J_{wR}$ correspond to the wing length. In a sanitary napkin of the type shown, the rear wing junctions 21, 22 are spaced further outboard of the longitudinal centerline as compared to the front wing junctions 19, 20. Consequently, the left and right wing junction lines $J_{wL}$ and $J_{wR}$ are not parallel to the longitudinal centerline A. However, the rear wing junctions 21, 22 may also be spaced such that the transverse distance between the rear wing junctions 21, 22 and the longitudinal centerline A is equal to the transverse distance between the front wing junctions 19, 20 and the longitudinal centerline A. In such an embodiment, the left and right wing junction lines $J_{wL}$ and $J_{wR}$ are parallel to the longitudinal centerline A. In a sanitary napkin of the type shown, the left and right wing junction lines $J_{wL}$ and $J_{wR}$ have a length of 50-110 mm, preferably between 75-100 mm, and most preferably between 85-95 mm.

The left and right wing 16, 17 further comprise a front wing distance point $D_{fl}$, $D_{fr}$ and a rear wing distance point $D_{rl}$, $D_{rr}$ located on the outer edge 38 of the left and right wing 16, 17. The front and rear wing distance points are spaced apart from the wing junction line $J_{wl}$ in an outboard transverse direction by a transverse distance $J_1$ of 3 mm. To determine the location of the front and rear wind distance point, one should proceed as follows: an imaginary line $K_L$, $K_R$ is drawn parallel to the wing junction line $J_{wL}$, $J_{wR}$ at a distance J1 of 3 mm outboard of the respective wing junction line $J_{wL}$, $J_{wR}$. The intersection of the imaginary line $K_L$, $K_R$ with the outer edge 38 on the forward side of the left and right wing determines the left and the right front wing distance points $D_{fl}$, $D_{fr}$ respectively. Similarly, the intersection of the imaginary line $K_L$, $K_R$ with the outer edge 38 on the rearward side of the left and right wing determines the left and the right rear wing distance points $D_{rl}$, $D_{rr}$ respectively.

The presence of the neck region 13 allows the disposable hygiene article 1 to bend more easily in a transversal direction x in the area of the neck portion. Since the left and right wing 16, 17 secure the disposable hygiene article 1 in the crotch region of the underwear of the user, the position of the left and right front wing distance points $D_{fl}$, $D_{fr}$ in relation to the neck determines the position of the neck portion in the user's underwear. As shown in FIG. 3, the left and the right front wing distance points $D_{fl}$, $D_{fr}$ are spaced from the neck region 13 of the absorbent core 6 in a rearward longitudinal direction by a first longitudinal distance D1. In a sanitary napkin of the type shown, the distance D1 is between 5-30 mm, more preferably between 10-20 mm. Such a configuration enables the disposable hygiene article 1 to better conform to the body shape of the user in the area where the front portion 2 transitions into the crotch portion 3. In embodiments where the neck region 13 comprises straight left and right core edge lines (8, 9) such that the neck extends in the longitudinal direction, the distance D1 is determined with reference to the part of the neck region located closest to the front wing distance point $D_{fl}$, $D_{fr}$ in the longitudinal direction. Typically, the width M between the left and the right core edge lines in the neck region is between 30-60 mm, preferably between 32-42 mm.

The crotch portion 3 of the article 1 is located adjacent to the front portion 2 in the longitudinal direction. In use, the crotch portion 3 lies between the legs of the user and covers a female user's genital region. In a sanitary napkin of the type shown in FIG. 1, the crotch portion 3 has a length b2 in the longitudinal direction which is between 25-60%, more preferably between 30-55%, most preferably between 30-50% of the total length b of the article. Typically, the length b2 of the crotch portion 3 in the longitudinal direction y is between 60-150 mm, such as between 80-120 mm. As shown in FIG. 1, the disposable hygiene article 1 has a front wing junction width $W_{fwj}$, measured in the transverse direction between the left and the right front wing junction, which is between 75-95 mm, more preferably between 80-90 mm and most preferably between 85-87 mm. The disposably hygiene article 1 further has a rear wing junction width $W_{rwj}$, measured in the transverse direction between the left and the right rear wing junctions 21, 22, which is between 85-95 mm, more preferably between 87-93 mm, and most preferably between 88-91 mm.

Figure 2:
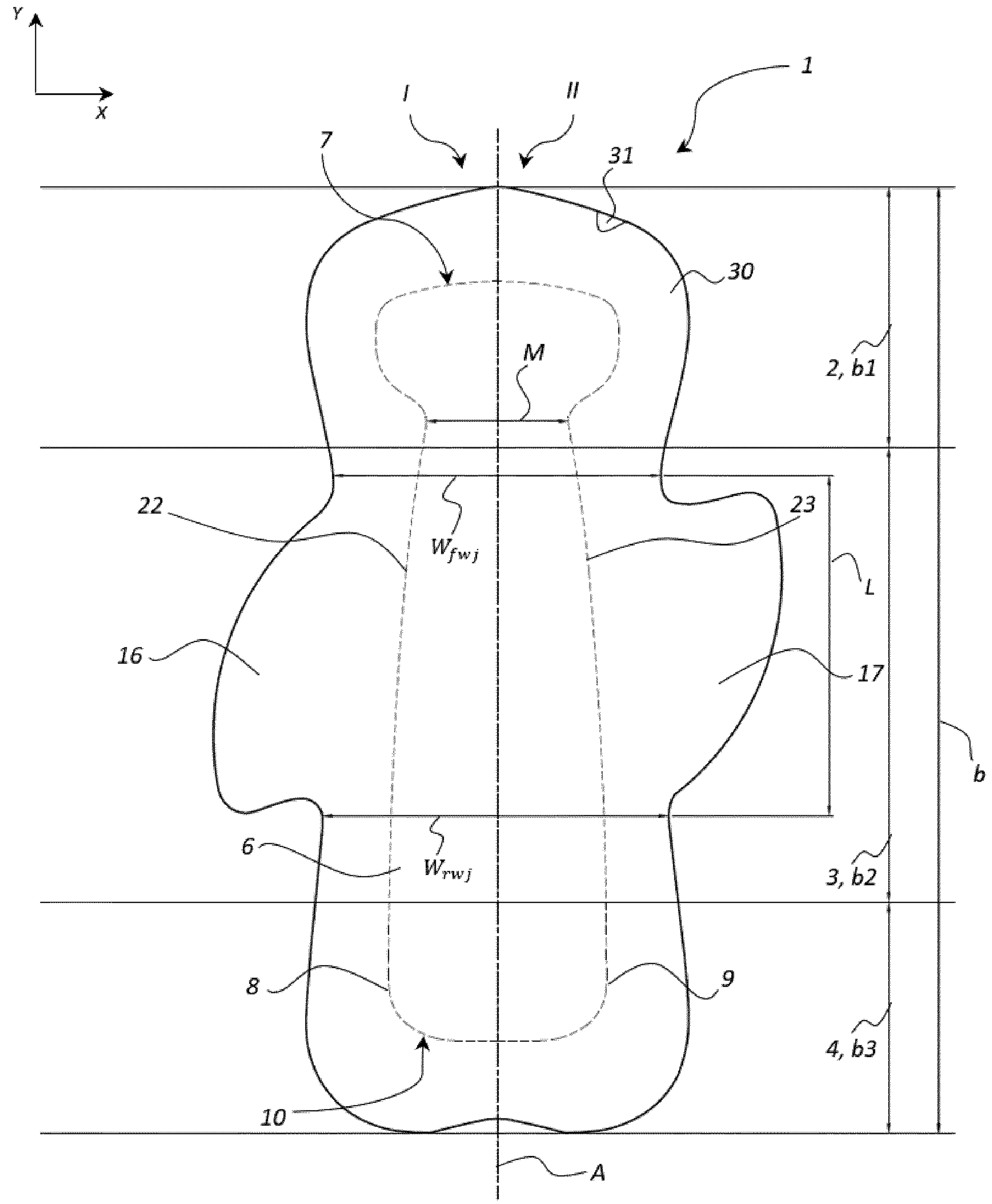
FIG. 2 shows schematically a plan view of a further exemplary disposable hygiene article according to the present disclosure.

The disposable hygiene article 1 in FIG. 1 comprises a left and right wing 16, 17 which are asymmetrical in shape with respect to any transverse axis extending in the transverse direction. Turning now to FIG. 2, the left and the right wings 16, 17 may also be asymmetrically shaped along the longitudinal centerline (A) and with respect to each other. The left and right wing 16, 17 in FIG. 2 are furthermore symmetrically disposed with respect to each other along a diagonal axis extending in a directing D in the plane of the sanitary article and with an angle α within the range of from 10° to 65° with respect to the longitudinal centerline A of the disposably hygiene article 1, such as for example within the range of from 30° to 55°. Hence, as may be seen in this FIG. 2, the left wing 16 may be a mirror-image of the right wing 17 if the left wing 16 is turned 180°.

Figure 4:
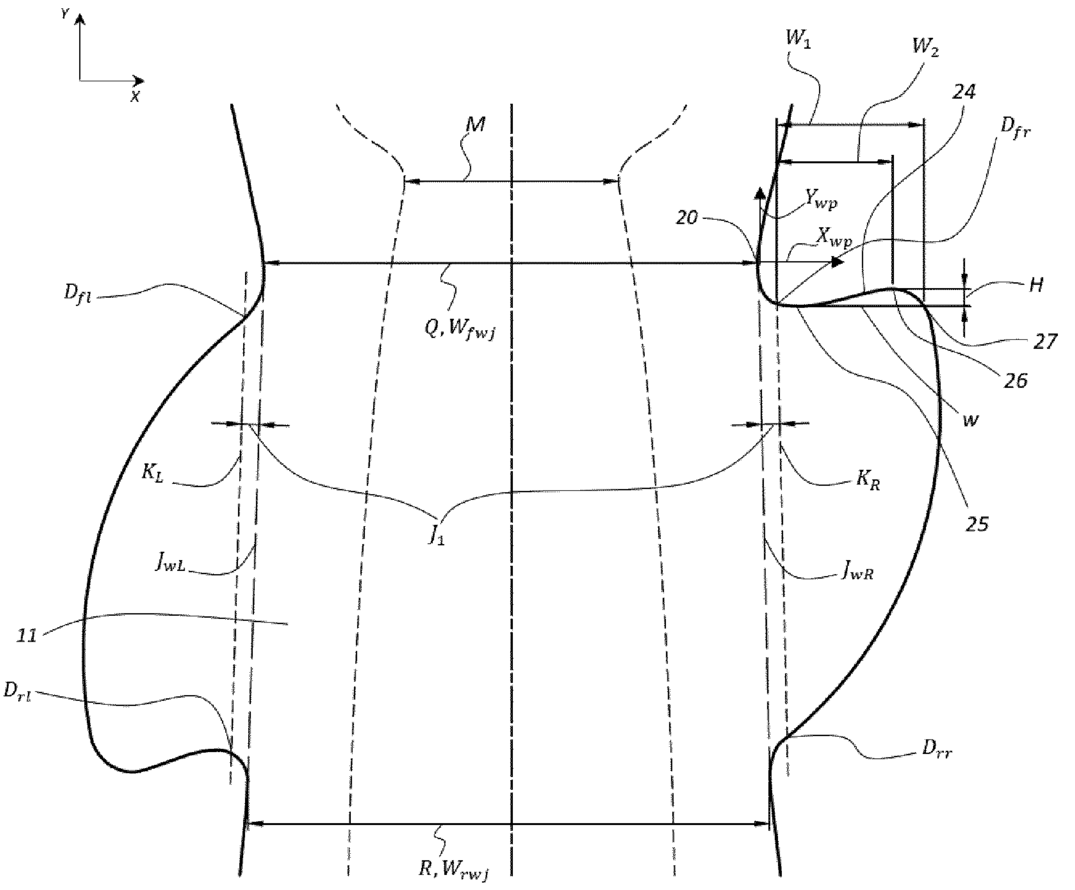
FIG. 4 shows schematically an enlarged view of a portion of a further exemplary disposable hygiene article according to the present disclosure.

The right wing in FIG. 4 is formed with an outer edge 38 comprising a wing positioning profile 24 coinciding with a section of the outer edge. The wing positioning profile 24 is formed from a wave starting from the right front wing junction 20 and extending outwards, the wave consisting of a concave curve having a through 25 and followed by a convex curve having a peak 26. The wave has a baseline $X_{wp}$ and a longitudinal axis $Y_{wp}$ perpendicular to the baseline $X_{wp}$. The wing positioning profile 24 ends at a wing positioning profile end point 27 where said wave no longer coincides with the outer edge 38. As shown in FIG. 4, the wing positioning profile end point 27 is defined as the intersection of the wing outer edge 38 with a straight line w starting from the trough of the concave cure and running parallel to the baseline $X_{wp}$. The concave curve and the convex curve may have the same wavelength and amplitude, or the wavelength and amplitude may differ in the concave versus the convex curve. In FIG. 4, the peak 26 of the convex curve is located forwards of the trough 25 as seen in the longitudinal direction y. A distance W2 between the front wing distance point $D_{fr}$ and the peak 26 of the convex curve of the wing positioning profile, as measured along the baseline $X_{wp}$, is between 10-30 mm, preferably between 10-25 mm, and most preferably between 12-22 mm. A distance W1 between the front wing distance point $D_{fr}$ and the wing positioning profile end point 27, as measured along the baseline $X_{wp}$, is between 15-35 mm, preferably between 18-28 mm. A shown in FIG. 4, the wing positioning profile 24 further has a height H measured between the trough 25 of the concave curve and the peak 26 of the convex curve along the longitudinal axis $Y_{wp}$. In a sanitary napkin of the type shown, the height H is between 1-5 mm.

Figure 5:
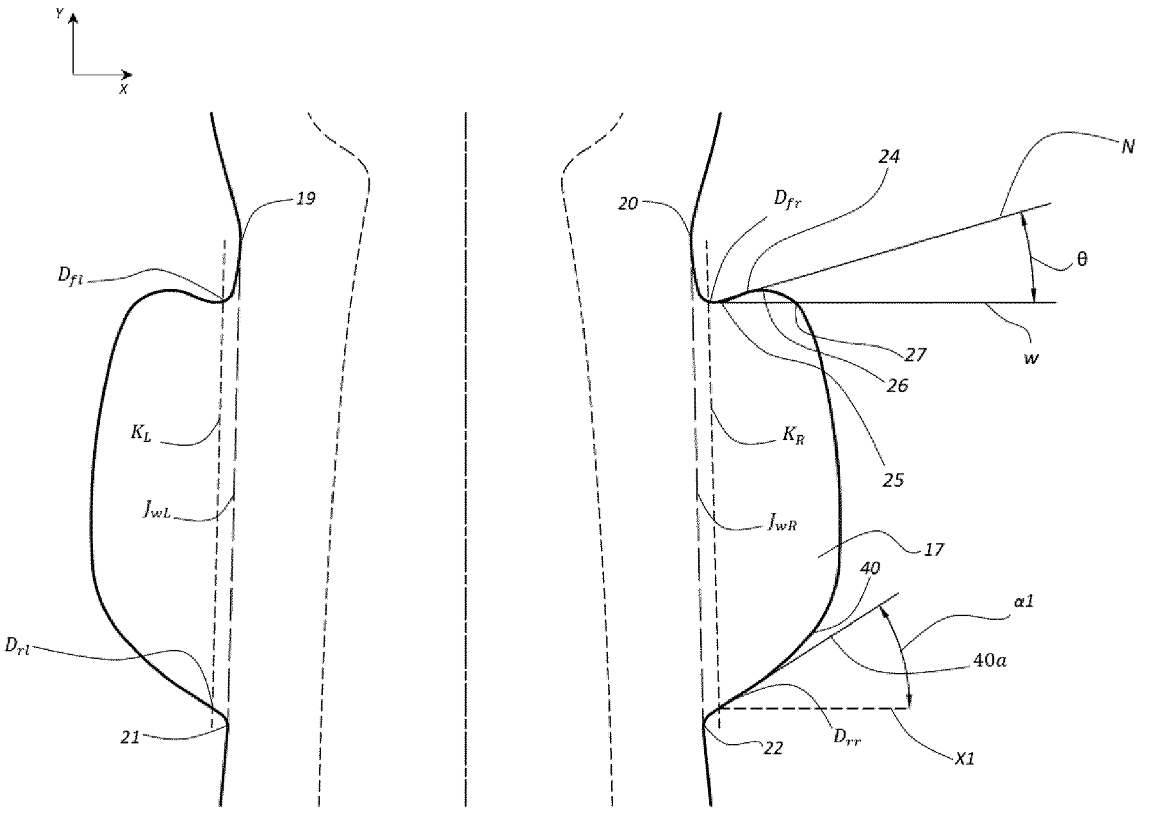
FIG. 5 shows schematically an enlarged view of a portion of a further exemplary disposable hygiene article according to the present disclosure.

In FIG. 5, the wing 17 defines an imaginary straight line N along a section of the wing positioning profile 24. The imaginary straight line N starts from the trough 25 of the wave and extends outboard along a section of the wing positioning profile 24, thus defining an angle θ with respect a straight line w starting from the trough of the concave cure and running parallel to the baseline $X_{wp}$, the magnitude of the angle θ being between +5 and +25 degrees, preferably between +8 and +20 degrees and most preferably between +10 and +17 degrees. Alternatively, the angle θ may have a negative magnitude of between −5 and −25 degrees, preferably between −8 and −20 degrees and most preferably between −10 and −17 degrees.

In FIG. 5, an imaginary straight line 40*a* starts from the rear wing distance point $D_{rr}$ extending in an outboard direction along a rear section 40 of the outer edge of the wing 17. The imaginary straight line 40*a* defines an angle α1 with respect to the transverse axis X1 running through the rear wing distance point $D_{rr}$ and perpendicular to the longitudinal centerline A. In a sanitary napkin of the type shown, the magnitude of the angle is between 30-60 degrees thus allowing for the creation of wings with longer longitudinal side edges while at the same time promoting optimal placement of the sanitary napkin in the underwear. Further, the longer longitudinal side edges provide for better protection against leakage along the longitudinal side edges of the disposable hygiene article 1. In FIG. 5, the angle α1 defined by the rear wing distance point $D_{rr}$ and the angle θ defined by trough 25 of the wave of the wing positioning profile are both between 30-60 degrees which creates a perception of forward direction. The perception of forward direction is a visual cue to the user to place the disposable hygiene article 1 more towards the front of the underwear such that the point of wetness is optimally located in relation to the user. However, the angle α1 may also be between 5 and 30 degrees which allows for a more defined folding line such that the user may more easily fold the wings of the disposable hygiene article 1 around the crotch region of the underwear.

Figure 6:
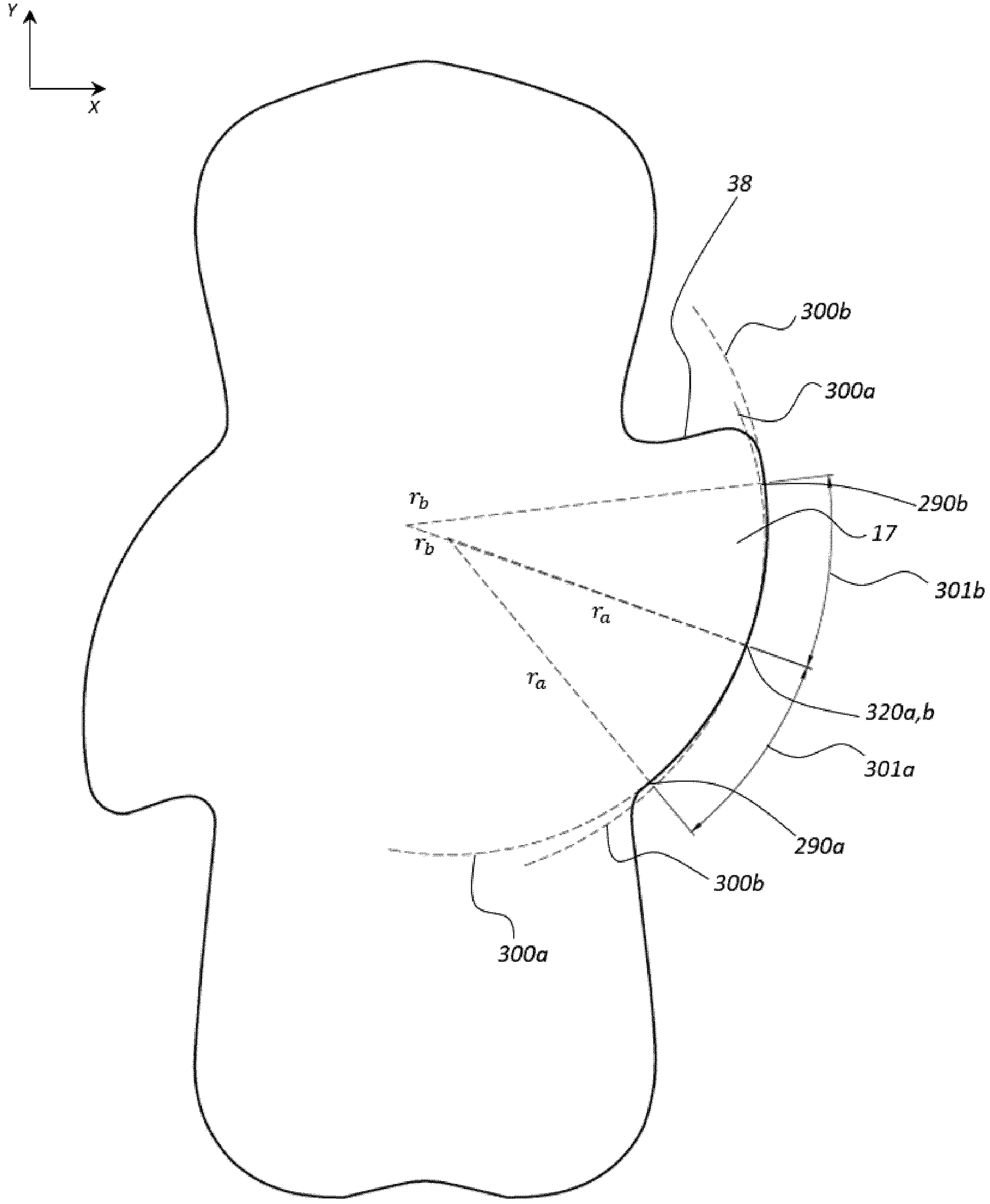
FIG. 6 shows schematically a plan view of a portion of a further exemplary disposable hygiene article according to the present disclosure.
Figure 7:
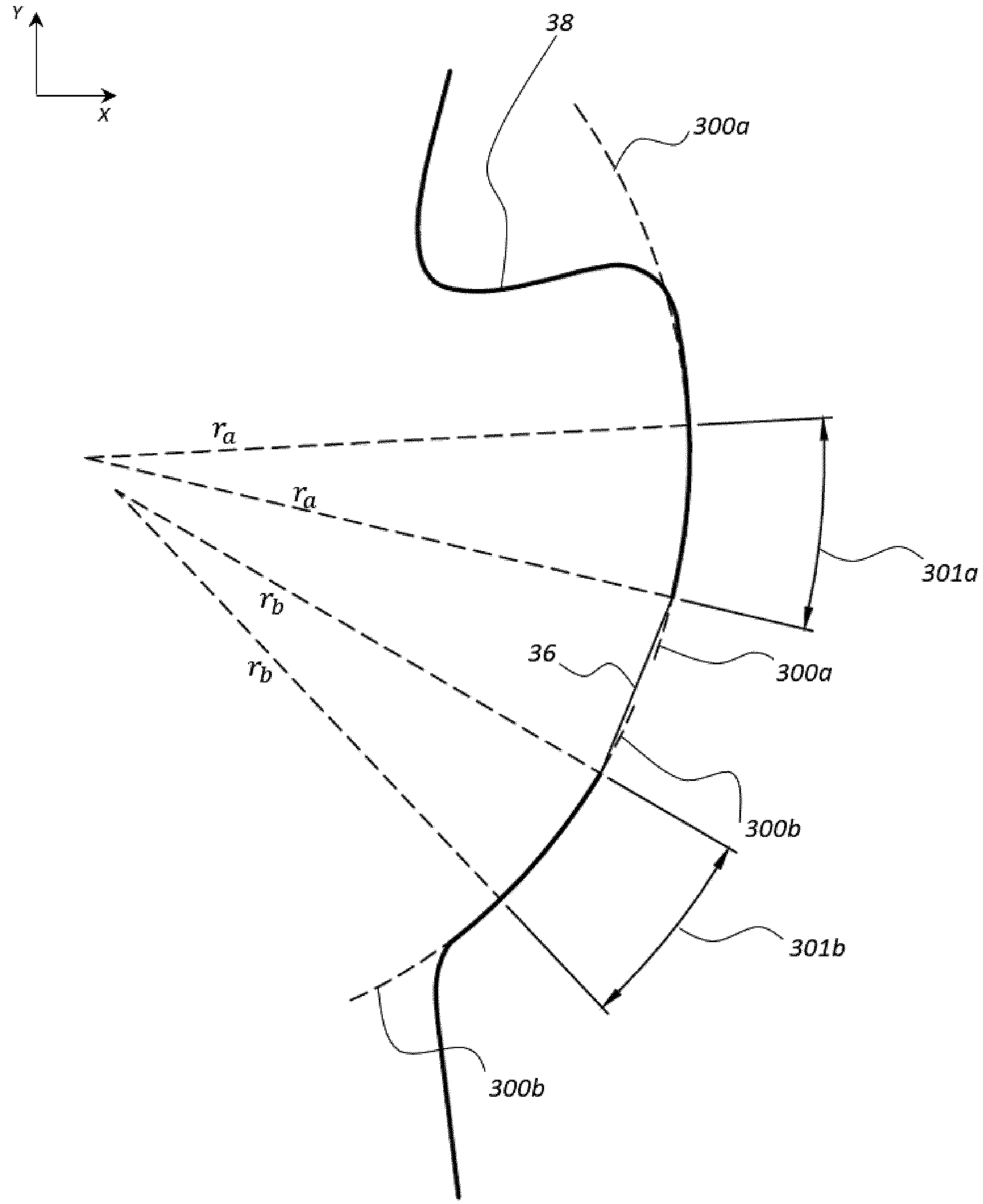
FIG. 7 shows schematically an enlarged view of a wing of a disposable hygiene article according to the present disclosure.

The outer edge 38 of the wing 17 in FIG. 6 comprises a rounded section 301*a* formed with an arc 300*a* of a circle with a defined radius ra and coinciding with the rounded section 301*a*. The rounded section 301*a* extends between a first point 290*a* of the outer edge 38 and a second point 320*a* along said outer edge 38 where the arc 300*a* no longer coincides with the outer edge 38. In a sanitary napkin of the type shown, the radius ra is within the interval of 40-500 mm. As illustrated in FIG. 6, the outer edge 38 of the wing 17 may further comprise a second rounded section 301*b*. The second rounded section 301*b* in FIG. 6 is formed with an arc 300*b* of a circle with a defined radius rb and coinciding with the rounded section 301*b*. The second rounded section 301*b* extends between a first point 290*b* of the outer edge 38 and a second point 320*b* where the arc 300*b* no longer coincides with the outer edge 38. Both the radius of the first and the second arch are within the interval of 40-500 mm. In FIG. 7, the outer edge 38 of the wing 17 further includes a straight section 36. The outer edge 38 may further comprise additional straight sections.

Generally, each of the fastening wings—referred to as "wings" in the present disclosure" 16 and 17 is provided with fastening means in the form of at least one adhesive area which is applied on the underside of each wing 16, 17, i.e. on the side which does not face the wearer.

The advantages of the present invention can be achieved with minimal disruption to or modification of known manufacturing techniques. In a production method suitable for manufacturing articles according to the invention, a liquid-permeable topsheet material layer, a liquid-impermeable backsheet material layer, and an absorbent material layer are fed into the manufacturing equipment. The core is arranged to be positioned in between the topsheet material layer and the backsheet material layer. An optional acquisition material layer is arranged to be positioned between the topsheet material layer and the absorbent material layer. In FIG. 1, the backsheet is assigned reference numeral 31, and the topsheet numeral 30. The absorbent core is assigned reference numeral 6. Suitable materials for the backsheet, topsheet 30 and absorbent core will be apparent to the person skilled in the art.

The disposable hygiene article of the present disclosure comprises an absorbent core, which is indicated in the figures with reference sign 6. The "absorbent core" is the absorbent structure of the article which acquires and stores bodily fluids. The absorbent core may be of any conventional kind. Examples of commonly occurring absorbent materials are cellulosic fluff pulp, tissue, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fibre, flake, sphere, etc. possesses a higher crosslink density than the inner portion of the superabsorbent. The superabsorbent materials may be in any form suitable for use in absorbent composites including particles, fibres, flakes, spheres, and the like. A high absorption capacity is provided by the use of high amounts of superabsorbent material. Thin absorbent cores which are common in for example sanitary napkins, baby diapers and incontinence guards, often comprise a compressed, mixed or layered structure of cellulosic fluff pulp and superabsorbent polymers. The size and absorbent capacity of the absorbent core may be varied to suit different product types, such as sanitary napkins for adult incontinent persons or panty liners.

Generally, the core can be of unitary construction, whereby for example the manufacturing process can be simplified. The phrase "unitary construction" in the present context is intended to mean that the absorbent core is constructed from essentially one type of material, this being essentially the same material, or essentially the same combination of two or more materials throughout the absorbent core. Variations in density and concentration of the material may occur, but these are limited to those which may be obtained without incorporation of regions which have been formed separately and then physically joined to each other. For example, when the absorbent core comprises a matrix of hydrophilic fibres and superabsorbent material as described above, the relative concentrations of superabsorbent material and fibres may be different in different parts of the core. However, the absorbent core of unitary construction does not comprise layers or laminates of different composition.

Likewise, variations in the density or concentration of various components across the longitudinal direction, the transverse direction or the thickness direction of the absorbent core are acceptable, yet the core should not comprise areas or layers of different composition which are formed separately and later joined together.

A suitable technique for manufacturing the absorbent cores of the present disclosure is mat-forming through an air-laying process. In the process an air-permeable mould is provided. Fibrous material is air-laid into the mould and the mould is filled, whereby an absorbent core is produced in with a desired amount of fibrous material.

Generally, the absorbent core 6 has an asymmetrical shape in the longitudinal extension y, but the first and second longitudinal portions I, II are symmetrical in the transverse extension x about the centre line A. The core 6 may have different shapes, but the circumferential edges of the core 8,9 define a shape in which a head portion 14 and at least one neck area, i.e. an area with smaller width in the transverse direction x, is located in the front portion 2 or in the transition area 5 of the core 6. In this way, the article 1 can better conform to the body shape in the area where the front portion 2 transitions to the crotch portion 3. Practically this means i.a. that the article 1 can bend in a transversal direction x more easily in the area of the neck portion. Therefore, the front portion 2 and the core head portion 14 can bend towards the user and thus the front portion 2 can better cover the pubic regions of the wearer while the crotch portion 3 is able to locate close to the genital area of a female wearer. Also the article 1 will better be held in its position during the use. Furthermore, and referring again to FIG. 2, since the width M of the neck portion essentially corresponds to the distance between the two mentioned muscle tendons on the wearer, the absorbent article 1 can during use be anchored firmly with the point of narrowest width M or transition 5 between the muscle tendons and be retained in this position. The front portion 2 of the article 1 is therefore held in the area in front of the mentioned muscle tendons, while the crotch portion 3 of the article 1 is effectively positioned correctly against the genitals of the wearer. This helps to avoid problems associated with incorrect placement of the absorbent article 1, or movement of the article 1 during wear. In this way, the article 1 is prevented from moving backwards between the legs of the wearer. Even though a sanitary towel is fastened to the underwear in use, this is a common problem in conventional sanitary towels because the leg movements of the wearer often shift the sanitary towel backwards.

Figure 8:
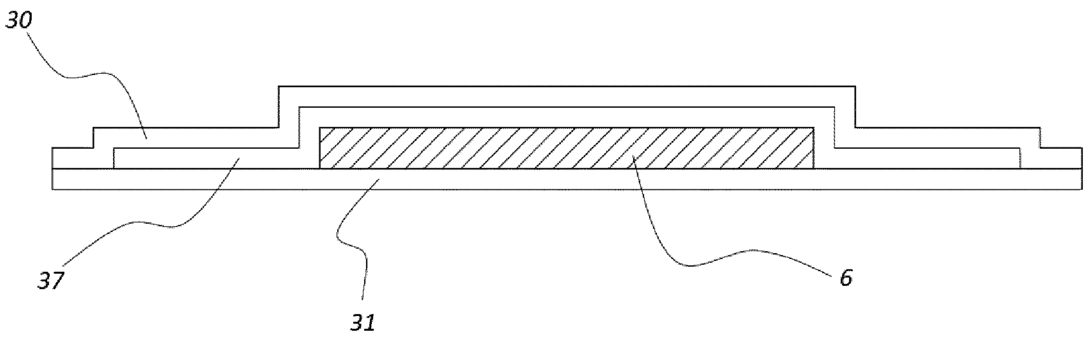
FIG. 8 shows schematically a transverse cross-sectional view of an exemplary disposable hygiene article according to the present disclosure.

FIG. 8 shows a cross-sectional view of the article of FIG. 1-7. The cross-sectional view of FIG. 8 clearly shows the topsheet 30, the backsheet 31, and the core 6 disposed therebetween. The liquid acquisition sheet 37 is provided between the core 6 and the topsheet 30. Preferably the liquid acquisition sheet 37 has have a larger extension in both the transverse x and longitudinal extension y of the core 6. In this way it is possible to obtain soft side edge areas. Preferably, the liquid acquisition sheet extends beyond the outer edges of the core 6 by approximately 1-15 mm. This means that the core is completely covered by the liquid acquisition sheet. Leakage control can be obtained since the liquid acquisition sheet 37 creates a fast inlet to trap the liquid in the product. E.g. at least a part of e.g. menstrual fluid in the areas outside the core is trapped whereby the fluid will thus not leak outside the hygiene article 1. In alternative embodiment, the liquid acquisition sheet 37 can be omitted.

The absorbent article 1 according to the present disclosure may include a liquid acquisition sheet 37, which acts as a liquid distribution layer. The acquisition layer 37 can have different shapes, and can be adapted to suit the shape of the absorbent core. The acquisition layer 37 may extend 1-15 mm beyond the outer edge of the core 6 (preferably around the entire periphery of the core 6). In some embodiments, the acquisition layer 37 may extend up to 50 mm in certain regions of the absorbent article 1. This configuration can provide neat edges at the periphery of the article. The liquid acquisition sheet 37 is located between the topsheet 30 and the core 6 and is suitably placed on top of the absorbent core. The liquid acquisition sheet 37 is adapted to quickly receive and temporarily store discharged liquid before it is absorbed by the absorbent core 6. Such acquisition distribution layers may be composed of for example airlaid nonwoven, spunlace nonwoven, high loft nonwoven or foam materials. The nonwoven material may be hydrophilic. A hydrophilic material may be obtained by adding a surfactant.

An air laid nonwoven can be produced with fluff, wood pulp, and here the fluff fibres are dispersed into a fast-moving air stream and condensed onto a moving screen by means of pressure and vacuum. The web can be bonded with resin and/or thermal plastic resin dispersed within the pulp. The web can be thermobonded (by heat), latex bonded (with adhesive) or multibonded (a combination of thermo and latex bonding) or mechanically bonded (high compression and temperature, bonding by hydrogen). The grammage of the airlaid nonwoven can suitably be from 50 to 100 gsm.

A high loft material is a nonwoven material and may be substantially free from absorbing fibres and superabsorbent material. The high loft nonwoven material may comprise thermoplastic polymer fibres, and may be selected from but not limited to, polyesters, polyamides and polyolefins such as polyethylenes (PE) and polypropylenes (PP), and may be a mixture of any of these. The high loft material refers to low density bulky fabrics, as compared to flat, paper-like fabrics. High loft webs are characterised by a relatively low density. This means that there is a relatively high amount of void space between the fibres. The high loft nonwoven fibrous layer of the invention may typically have a density below 0.200 g/cc (200 kg/$m^3$), in particular ranging from 0.015 g/cc to 0.150 g/cc (15 kg/$m^3$ to 150 kg/$m^3$), in particular from 0.030 g/cc to 0.100 g/cc (30 to 100 kg/$m^3$), for example 0.065 g/cc (65 kg/$m^3$). The average density can be calculated by dividing the basis weight of the high loft layer by its thickness measured at a pressure of 0.5 kPa (see the method details further below). Normally the thickness of high loft materials is more than about 0.5 mm, such as more than 1 mm or suitably 1.5-2.0 mm, and the solid content is low, usually less than 15% by volume. The high loft nonwoven layer may advantageously be a spunmelt nonwoven. Spunmelt is a generic term describing the manufacturing of nonwoven webs directly from thermoplastic polymers. It encompasses 2 processes and the combination of both: spunlaid (also known as spunbond) nonwoven and meltblown nonwoven. In a spunlaid process, polymer granules are melted and molten polymer is extruded through spinnerets. The continuous filaments are cooled and deposited on to a conveyor to form a uniform web. Some remaining temperature can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it and breaks it up into a fibrous web. The liquid acquisition sheet material may be of a spunbonded material and may be a spunbond-meltbond-spunbond (SMS) material. The high loft nonwoven layer may in particular have a thickness ranging from 0.30 mm to 2.00 mm, for example 1.0 mm as measured at a pressure of 0.5 kPa (according to the test method referred to in PCT Application No. PCT/SE2017/050612). The grammage, i.e. basis weight of the high loft material may for example range from 15 gsm to 500 gsm, in particular from 30 gsm to 200 gsm, such as 30-90 gsm, for example 64 gsm.

According to a further variant, the liquid acquisition sheet 37 is a spunlace, also referred to as spunbond, nonwoven material. A spunlace nonwoven product is derived from a process of entangling a web of loose fibres through multiple rows of jets of water at high pressure; this process entangles the fabrics and interlinks the fibres. There are several terms for spunlace nonwoven fabric or spunlaced, such as jet entangled, needled, hydroenentangled or hydraulic, but the term spunlace or spunlaced is the most popular in the nonwoven industry. The raw material for the acquisition sheet can be polypropylene (PP), polyethylene (PE) polyester (PET), polyamide (PA), cellulosic fibres or a combination of these and different weights and compositions are possible, such as viscose, polyester, cotton, nylon and microfibre, wherein viscose is the most commonly used raw material. Thus, if a combination of different fibres is used, this can be a mixture of fibres from different polymers, although each fibre can also include different polymers (e.g. PP/PE bi-component fibres or PP/PE copolymers). Where appropriate, the plastic film can consist of PE or PP, PET, PLA or amyl (or, for that matter, any other thermoplastic polymer), or a mixture or copolymers of the aforementioned polymers. The spunlace material usually comprises polypropylene or polyethylene fibres which provide for optimal comfort for the nonwoven material. Other suitable fibres for making the nonwoven material are for example natural fibres such as bamboo, cotton and flax. The grammage of the spunlace nonwoven material can be typically from 30-80 gsm.

The topsheet may include or consist of fibrous nonwoven layer(s) being spunbonded, meltblown, carded, hydroentangled, wetlaid. Suitable nonwoven materials can be composed of natural fibers, such as woodpulp or cotton fibers, synthetic thermoplastic fibers, such as polyolefins, polyesters, polyamides and blends and combinations thereof or from mixtures of natural and synthetic fibers. The materials suited as topshet material should be soft and non-irritating to the skin and be readily penetrated by body fluid, such as menstrual fluid and urine.

The backsheet may consist of a thin plastic film, e.g. a polyethylene or polypropylene film, a nonwoven material coated with a liquid impervious material, a hydrophobic nonwoven, which resist liquid penetration. Laminates of plastic films and nonwoven materials may also be used. The backsheet material can be breathable to allow vapor to escape from the absorbent structure, while still preventing liquids from passing through the backsheet material.

The wing may consist of a separate material attached to the longitudinal side edges of the outer periphery 18 of the disposable hygiene article 1. A suitable material may be any of the materials listed above in connection with topsheet and backsheet. Alternatively, the wing may consist of an extension of the topsheet or backsheet material, or both.

Although not shown in the figures, the absorbent article 1 defined above may comprise any attachment means known in the art to allow fastening to undergarments of a wearer. Such means may include a coating of adhesive or friction coating on the garment-facing surface of the article. Furthermore, the article 1 according to the invention comprises attachment flaps ("wings") which extend in the transverse direction of the article 1 and are intended to be arranged around the crotch portion on the briefs of the wearer. It is however important that the nature and placement of such attachment means does not significantly interfere with the function of the article 1 in use.

The sanitary article according to the present disclosure may thus be provided with an adhesive, such as a pressure-sensitive adhesive on the backsheet. The elongated wrapping sheet may be releasably adhered the adhesive-bearing backsheet of the sanitary article. The wrapping sheet may be coated with material which enables the release of the wrapping sheet, such as silicone, so that the wrapping sheet may be peeled away from the adhesive-bearing backsheet of the sanitary article and so that the sanitary article may be attached to an undergarment. The adhesive-bearing region of the backsheet may also be covered with a release paper. The release paper may be attached to the wrapping sheet, for example with a permanent attachment, such that the sanitary article is attached to the wrapping sheet via the release paper.

The invention claimed is:

1. A disposable hygiene article defining a transverse direction and a longitudinal direction, comprising:
- a liquid-permeable topsheet;
- a liquid-impermeable backsheet; and
- an absorbent core arranged between the topsheet and the backsheet,
- wherein a longitudinal centerline divides the disposable hygiene article into a left hand portion and a right hand portion,
- wherein the disposable hygiene article has a front portion, a crotch portion, and a rear portion,
- wherein the topsheet and the backsheet extend beyond the absorbent core to provide an outer boundary region of the disposable hygiene article that surrounds the absorbent core,
- wherein an outer contour of the absorbent core is defined by mutually symmetrical mirror-imaged portions arranged symmetrically about the longitudinal centerline, and defined by left and right core edge lines,
- wherein the absorbent core extends between a core front edge in the front portion and a core rear edge in the rear portion,
- wherein the absorbent core comprises a neck region at which a transverse width (M) between the left and right core edge lines is smaller than a transverse width of the absorbent core forward of the neck region, and a transverse width rearward of the neck region,
- wherein the absorbent core comprises a head region forward of the neck region and a body portion rearward of the neck region,
- wherein the disposable hygiene article further comprises at least one asymmetrical wing as seen along any transverse axis of the disposably hygiene article,
- wherein the asymmetrical wing comprises an outer edge extending in an outward direction from the outer periphery of the disposable hygiene article,
- wherein the outer edge of the at least one asymmetrical wing meets the outer periphery of the disposable hygiene article at front and rear wing junctions connected via a wing junction line $J_w$, wherein the outer edge of the at least one asymmetrical wing comprises a front wing distance point $D_f$ and a rear wing distance point $D_r$, wherein the front wing distance point $D_f$ is spaced from the junction line $J_w$ in an outboard transverse direction by a transverse distance J1 of 3 mm, wherein the front wing distance point $D_f$ is spaced from the neck region in a rearward longitudinal direction by a first longitudinal distance D1 of 10-25 mm, wherein the transverse width of the neck region is a minimum transverse width of the absorbent core, and wherein the neck region of the absorbent core is positioned forward of a minimum width portion of the disposable hygiene article forward of the at least one asymmetrical wing.

2. The disposable hygiene article according to claim 1, wherein the outer edge comprises a wing positioning profile coinciding with a section of the outer edge, wherein the wing positioning profile is formed from a wave having a baseline $X_{wp}$ and a longitudinal axis $Y_{wp}$ perpendicular to the baseline $X_{wp}$, said wave starting from the front wing junction and extending outwards, the wave consisting of a concave curve having a trough and a convex curve having a peak, the wing positioning profile ending at a wing positioning profile end point where said wave no longer coincides with said outer edge.

3. The disposable hygiene article according to claim 1, wherein said wing junction line $J_w$ corresponding to the wing length is between 50-110 mm.

4. Disposable hygiene article according to claim 1, wherein the width M between the left and right core edge lines in the neck region is between 30-60 mm.

5. The disposable hygiene article according to claim 1, wherein a front wing junction width $W_{fwj}$ between the left and the right front wing junctions, as seen along the transverse axis, is between 75-95 mm.

6. The disposable hygiene article according to claim 1, wherein a rear wing junction width $W_{rwj}$ between the left and the right rear wing junctions, as seen along the transverse axis, is between 85-95 mm.

7. The disposable hygiene article according to claim 2, wherein the peak of the convex curve is located forward of the trough of the concave curve as seen in the longitudinal direction y.

8. The disposable hygiene article according to claim 2, wherein the baseline $X_{wp}$ of the wave is placed perpendicular on the longitudinal centerline A of the disposable hygiene article.

9. The disposable hygiene article according to claim 2, wherein a distance W2 between the front wing distance point $D_{fr}$ and the peak of the convex curve of the wing positioning profile, as measured along the baseline $X_{wp}$, is between 8-30 mm.

10. The disposable hygiene article according to claim 2, wherein a distance W1 between the front wing distance point $D_{fr}$ and the wing positioning profile end point, as measured along the baseline $X_{wp}$, is between 13-35 mm.

11. The disposable hygiene article according to claim 2, wherein a height H between the trough of concave curve and the peak of the convex curve of the wave, as measured along the longitudinal axis $Y_{wp}$ of said wave, is between 1-5 mm.

12. The disposable hygiene article according to claim 2, wherein said wing defines an imaginary straight line N along a section of the wing positioning profile, said imaginary straight line N starting from the trough of the concave curve and extending outboard, and wherein said imaginary straight line N defines an angle θ with respect to a straight line w starting from the trough of the concave cure and running parallel to the baseline $X_{wp}$, the magnitude of the angle being between +5 and +25 degrees.

13. The disposable hygiene article according to claim 2, wherein said wing defines a straight line N along a section of the wing positioning profile, said straight line starting from said front wing distance point $D_f$ and extending outboard, wherein said straight line defines an angle θ with respect to a straight line w starting from the trough of the concave cure and running parallel to the baseline $X_{wp}$, the magnitude of the angle being between −5 and −25 degrees.

14. The disposable hygiene article according to claim 2, wherein the outer edge of said wing further comprises a rounded section formed with an arc of a circle and coinciding with the rounded section and having a defined radius r, said rounded section extending between a first point of the outer edge and a second point along said outer edge where said arc no longer coincides with said outer edge, wherein said radius r is within an interval of 40-500 mm.

15. The disposable hygiene article according to claim 2, wherein the outer edge of said wing further comprises two or more rounded sections formed with an arc of a circle and coinciding with the rounded section, each of said first and second arcs having a defined first and second radius, said first radius being within an interval of 40-500 mm and said second radius being within an interval of 40-500 mm.

16. The disposable hygiene article according to claim 2, wherein said outer edge includes at least one straight section.

17. The disposable hygiene article according to claim 2, wherein said wing defines a lower straight line along a lower edge section, and wherein the lower straight line defines an angle with respect to a transverse axis X1 perpendicular to the longitudinal centerline A, the magnitude of the angle being between 30-60 degrees.

18. The disposable hygiene article according to claim 2, wherein said wing defines a lower straight line along a lower edge section, and wherein the lower straight line defines an angle with respect to a transverse axis X1 perpendicular to the longitudinal centerline A, the magnitude of the angle being between 5-30 degrees.

19. The disposable hygiene article according to claim 1, wherein said disposable hygiene article comprises a second asymmetrical wing as seen along any transverse axis of the disposably hygiene article, and wherein the first and the second asymmetrical wing are asymmetrical with respect to each other as seen along the longitudinal centerline.

20. The disposable hygiene article according to claim 1, wherein the neck region of the absorbent core is positioned forward of a transition between the front portion and the crotch portion of the disposable hygiene article with a distance between the neck region and the transition.

* * * * *